(12) United States Patent
Way et al.

(10) Patent No.: US 9,422,398 B2
(45) Date of Patent: Aug. 23, 2016

(54) COPOLYMER, AND METHOD FOR PREPARING A MONOMER USED TO FORM THE COPOLYMER

(71) Applicant: INDUSTRIAL TECHNOLOGY RESEARCH INSTITUTE, Hsinchu (TW)

(72) Inventors: Tun-Fun Way, Hsinchu (TW); Jiun-Jy Chen, Toufen Township, Miaoli County (TW); Cheng Yeh, Zhubei (TW); Yu-Ting Chen, Changhua County (TW)

(73) Assignee: INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 0 days.

(21) Appl. No.: 14/724,048

(22) Filed: May 28, 2015

(65) Prior Publication Data

US 2015/0344414 A1 Dec. 3, 2015

Related U.S. Application Data

(60) Provisional application No. 62/005,240, filed on May 30, 2014.

(30) Foreign Application Priority Data

May 25, 2015 (TW) .............................. 104116750 A

(51) Int. Cl.
| | | |
|---|---|---|
| *C08G 69/44* | (2006.01) | |
| *C08G 69/26* | (2006.01) | |
| *C08G 69/28* | (2006.01) | |
| *C07C 231/02* | (2006.01) | |
| *C08G 73/16* | (2006.01) | |

(52) U.S. Cl.
CPC .............. *C08G 69/44* (2013.01); *C07C 231/02* (2013.01); *C08G 69/265* (2013.01); *C08G 69/28* (2013.01)

(58) Field of Classification Search
CPC ........................... C07C 233/64; A23L 1/2364
USPC .................................................. 528/292, 337
See application file for complete search history.

(56) References Cited

U.S. PATENT DOCUMENTS

| | | |
|---|---|---|
| 4,120,928 A | 10/1978 | Furukawa et al. |
| 5,071,924 A | 12/1991 | Koch et al. |
| 5,126,401 A | 6/1992 | Chou |
| 5,393,902 A | 2/1995 | Coope et al. |
| 5,397,501 A | 3/1995 | Coope |
| 5,410,076 A | 4/1995 | Coope et al. |
| 5,482,998 A | 1/1996 | Muehlbach et al. |
| 5,571,874 A | 11/1996 | Hattori et al. |
| 5,760,143 A | 6/1998 | Kubo et al. |
| 5,770,654 A | 6/1998 | Blatz |

(Continued)

FOREIGN PATENT DOCUMENTS

| | | |
|---|---|---|
| CN | 1155628 C | 6/2004 |
| CN | 1646603 A | 7/2005 |

(Continued)

OTHER PUBLICATIONS

Cakir et al., "Incorporation of a semi-aromatic nylon salt into polyamide 6 by solid-state or melt polymerization," Polymer, vol. 53, 2012 (Available online Sep. 21, 2012), pp. 5242-5250.

(Continued)

*Primary Examiner* — Terressa Boykin
(74) *Attorney, Agent, or Firm* — Birch, Stewart, Kolasch & Birch, LLP

(57) ABSTRACT

A copolymer, and a method for preparing a monomer used to form the copolymer are provided. The copolymer is a reaction product of a first monomer and a second monomer. In particular, the first monomer has a structure represented by Formula (I), and the second monomer has a structure represented by Formula (II), Formula (III), or Formula (IV)

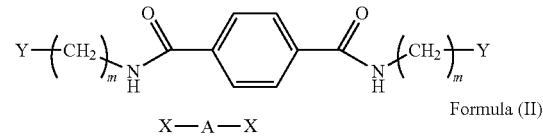

Formula (I)

X—A—X

Formula (II)

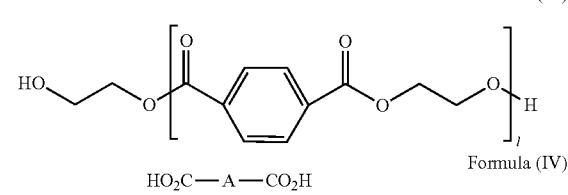

Formula (III)

HO₂C—A—CO₂H

Formula (IV)

wherein Y is —NH₂, or —CO₂H; m is a positive integer from 2 to 10; X is independently —NH₂, or —OH; A is $-(CH_2)_n$—,

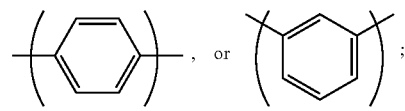

n is a positive integer from 2 to 10; and, l is a positive integer from 1 to 5.

16 Claims, No Drawings

(56) References Cited

U.S. PATENT DOCUMENTS

| | | | |
|---|---|---|---|
| 6,147,043 | A | 11/2000 | Moeller et al. |
| 6,696,165 | B1 | 2/2004 | Bennett et al. |
| 7,601,915 | B2 | 10/2009 | Lumachi et al. |
| 7,915,336 | B2 | 3/2011 | Varnhorn et al. |
| 7,927,710 | B2 | 4/2011 | Hewel |
| 8,633,148 | B2 | 1/2014 | Smets et al. |
| 2002/0026077 | A1 | 2/2002 | Collins et al. |
| 2002/0028857 | A1 | 3/2002 | Holy |
| 2005/0003987 | A1 | 1/2005 | Baker et al. |
| 2007/0036998 | A1 | 2/2007 | Dowe et al. |
| 2007/0149434 | A1 | 6/2007 | Baker et al. |
| 2008/0190643 | A1 | 8/2008 | Lumachi et al. |
| 2009/0247690 | A1 | 10/2009 | Varnhorn et al. |
| 2010/0000759 | A1 | 1/2010 | Lumachi et al. |
| 2011/0245134 | A1 | 10/2011 | Smets et al. |
| 2011/0245136 | A1 | 10/2011 | Smets et al. |
| 2012/0017947 | A1 | 1/2012 | Fernandez Prieto et al. |
| 2012/0028874 | A1 | 2/2012 | Fernandez Prieto et al. |
| 2013/0061883 | A1 | 3/2013 | Miravet Celades et al. |
| 2013/0245275 | A1* | 9/2013 | Famulok .............. A61K 31/341 546/323 |
| 2013/0261256 | A1 | 10/2013 | Ieda et al. |
| 2014/0107009 | A1 | 4/2014 | Smets et al. |

FOREIGN PATENT DOCUMENTS

| | | |
|---|---|---|
| CN | 1312192 C | 4/2007 |
| CN | 101466790 B | 4/2013 |
| TW | 200600342 A | 1/2006 |
| TW | 200848442 A | 12/2008 |

OTHER PUBLICATIONS

Rwei et al., "The crystallization kinetics of Nylon 6/6T and Nylon 66/6T copolymers," Thermochimica Acta, vol. 555, 2013 (Available online Jan. 10, 2013), pp. 37-45.

Samperi et al., "Structural Characterization of Copolyamides Synthesized via the Facile Blending of Polyamides," Macromolecules, vol. 37, No. 17, 2004 (Published on Web Jul. 29, 2004), pp. 6449-6459.

Wang et al., "Influence of Preparation Methods on the Structures and Properties for the Blends Between Polyamide 6co6T and Polyamide 6: Melt-mixing and In-situ Blending," Journal of Polymer Science: Part B: Polymer Physics, vol. 46, 2008, pp. 201-211.

Wang et al., "Melt polymerized aramid/polycaprolactam copolymer and its fiber," Polymer International, vol. 63, 2014, Accepted article published Jul. 1, 2013 (Published online Aug. 6, 2013), pp. 727-732.

Taiwan Office Action for Appl. No. 104116750 dated Apr. 7, 2016.

* cited by examiner

COPOLYMER, AND METHOD FOR PREPARING A MONOMER USED TO FORM THE COPOLYMER

CROSS REFERENCE TO RELATED APPLICATION

This application is based upon and claims the benefit of priority from the prior Taiwan Patent Application No. 104116750, filed on May 25, 2015, the entire contents of which are incorporated herein by reference.

This application claims the benefit of U.S. Provisional Application No. 62/005,240, filed on May 30, 2014, which provisional application is hereby incorporated herein by reference.

TECHNICAL FIELD

The disclosure relates to a copolymer, and method for preparing a monomer used to form the copolymer.

BACKGROUND

Nylon 6 is widely applied in daily life, such as clothes, furniture supplies, and other areas. However, the melting point, softening point, heat resistance, and mechanical properties of nylon 6 are less satisfactory than that of nylon 66. Nylon 6 is limited with these unfavorable characteristics to apply larger range products for a long time. Therefore, the chemical synthesis technique is applied to develop differentiated products to promote the additional value of nylon 6. The existing techniques for modifying nylon 6 still doesn't improve the properties of nylon 6 which has uniform molecular sequential distribution and high melting point.

SUMMARY

According to embodiments of the disclosure, the disclosure provides a copolymer, which is a reaction product of a first monomer and a second monomer, wherein the first monomer has a structure represented by Formula (I)

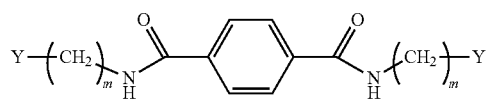

Formula (I)

wherein Y is —$NH_2$, or —$CO_2H$; m is a positive integer from 2 to 10; when Y is —$CO_2H$, the second monomer has a structure represented by Formula (II), or Formula (III), and when Y is —$NH_2$, the second monomer has a structure represented by Formula (IV)

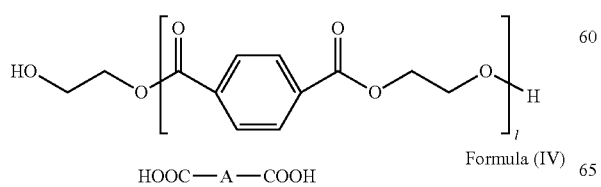

Formula (II)
Formula (III)
Formula (IV)

Wherein X is independently —$NH_2$, or —OH; A is —$(CH_2)_n$—,

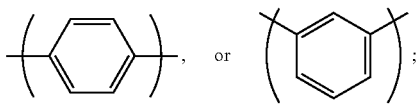

n is a positive integer from 2 to 10; and, l is a positive integer from 1 to 5.

According to another embodiment of the disclosure, the disclosure also provides a method for preparing a monomer includes: reacting a compound having a structure represented by Formula (VIII) and a compound having a structure represented by Formula (IX) via a melting reaction or a solution reaction; and, subjecting the reaction product of the melting reaction or the solution reaction to an acidification reaction to obtain the monomer having a structure represented by Formula (I)

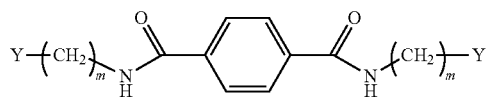

Formula (I)

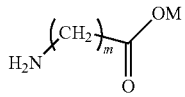

Formula (VIII)

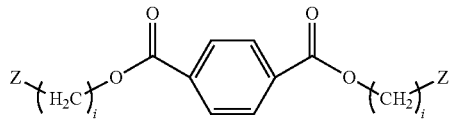

Formula (IX)

wherein M is Na, or K; m is a positive integer from 2 to 10; i is a positive integer from 1 to 3; Y is —$CO_2H$; and, Z is H or —OH.

A detailed description is given in the following embodiments with reference to the accompanying drawings.

DETAILED DESCRIPTION

The following description is of the best-contemplated mode of carrying out the disclosure. This description is made for the purpose of illustrating the general principles of the disclosure and should not be taken in a limiting sense. The scope of the disclosure is best determined by reference to the appended claims.

According to the embodiments of the disclosure, the disclosure provides a copolymer, which is a reaction product of a first monomer and a second monomer, wherein the first monomer has a structure represented by Formula (I)

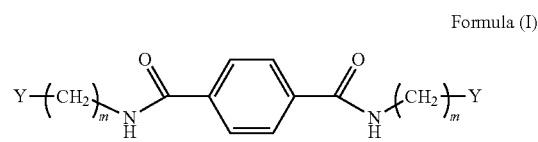

Formula (I)

wherein Y can be —NH$_2$, or —CO$_2$H, and m can be a positive integer from 2 to 10. When Y is —CO$_2$H, the second monomer may have a structure represented by Formula (II), or Formula (III), and when Y is —NH$_2$, the second monomer may have a structure represented by Formula (IV)

X—A—X     Formula (II)

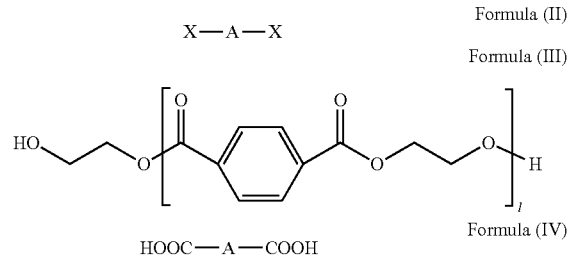

Formula (III)

HOOC—A—COOH     Formula (IV)

wherein X can be independently —NH$_2$, or —OH; A can be —(CH$_2$)$_n$—,

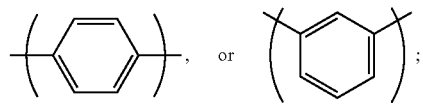

n can be a positive integer from 2 to 10; and, l can be a positive integer from 1 to 5.

According to the embodiments of the disclosure, the first monomer can be

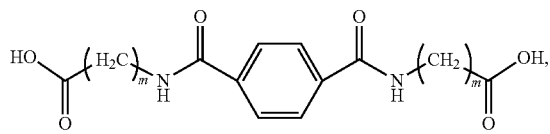

wherein m is a positive integer from 2 to 10. In addition, when the first monomer is

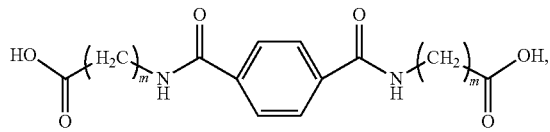

the second monomer may be H$_2$N-A-NH$_2$, wherein A is —(CH$_2$)$_n$—,

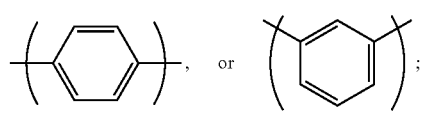

and, n is a positive integer from 2 to 10. For example, the second monomer can be

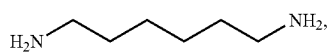

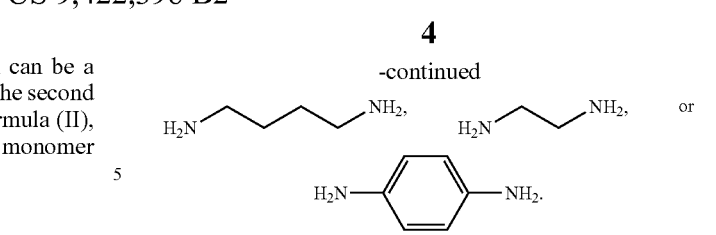

According to another embodiments of the disclosure, when the first monomer is

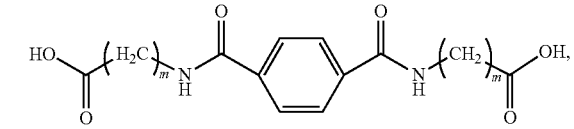

the second monomer can be

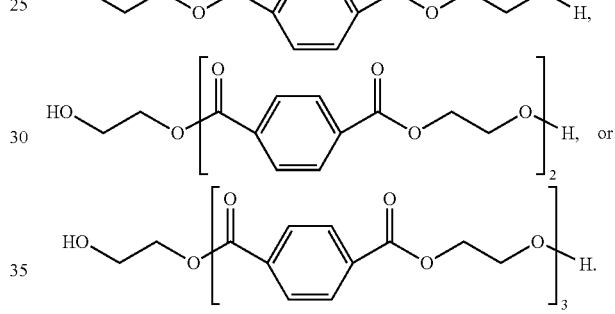

According to some embodiments of the disclosure, the first monomer may be

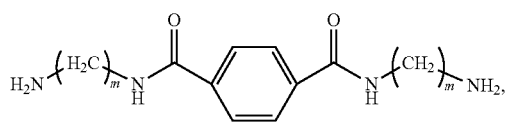

wherein m is a positive integer from 2 to 10. When the first monomer is

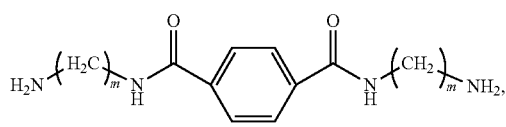

the second monomer can be

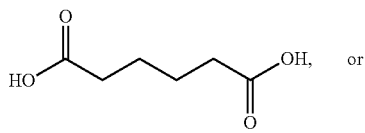

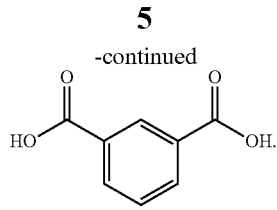

According to some embodiments of the disclosure, the copolymer may have a repeat units represented by Formula (V)

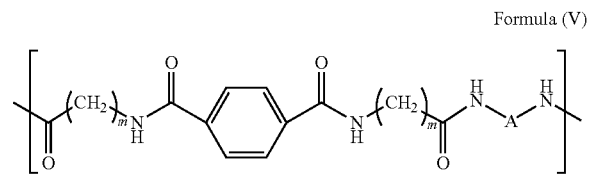

wherein A is $-(CH_2)_n$,

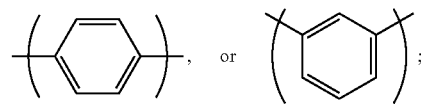

m is a positive integer from 2 to 10; and, n is a positive integer from 2 to 10.

According to some embodiments of the disclosure, the copolymer may have a repeat unit represented by Formula (VI)

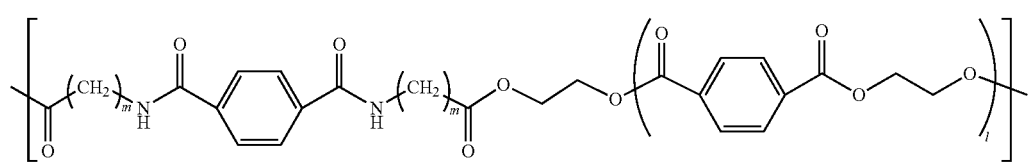

wherein m is a positive integer from 2 to 10; and, l is a positive integer from 1 to 5.

According to some embodiments of the disclosure, the copolymer may have a repeat unit represented by Formula (VII)

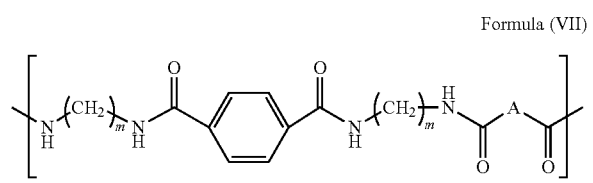

wherein A is $-(CH_2)_n$,

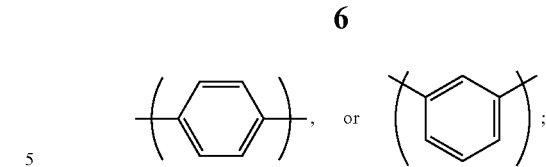

m is a positive integer from 2 to 10; and, n is a positive integer from 2 to 10.

According to the embodiments of the disclosure, the copolymer may have a melting temperature between 220° C. to 270° C., such as between 240 to 265° C.

According to the embodiments of the disclosure, the disclosure also provides a method for preparing the monomer which is used to form the above-mentioned copolymer. The method includes: reacting a compound having a structure represented by Formula (VIII) and a compound having a structure represented by Formula (IX) via a melting reaction or a solution reaction; and, subjecting the reaction product of the melting reaction or the solution reaction to an acidification reaction to obtain the monomer having a structure represented by Formula (I)

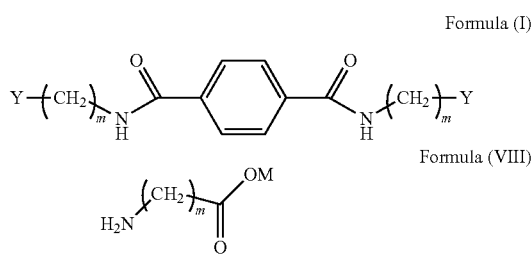

-continued

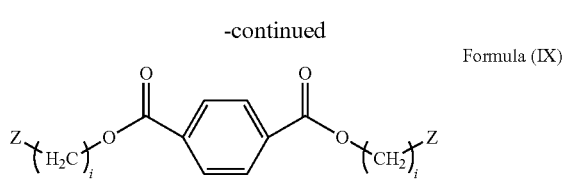

wherein M is Na, or K; m is a positive integer from 2 to 10; i is a positive integer from 1 to 3; Y is $-CO_2H$; and, Z is H or $-OH$.

According to some embodiments of the disclosure, subjecting the reaction product of the melting reaction or the solution reaction to an acidification reaction may include steps: mixing the reaction product and water to form a mixture; and titrating the mixture with an inorganic acid aqueous solution until that the mixture has a pH value between 5 and 7, such as between 5.6 and 6.4.

According to the embodiments of the disclosure, the compound having a structure represented by Formula (VIII) can be

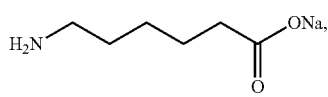

and the compound having a structure represented by Formula (IX) may be

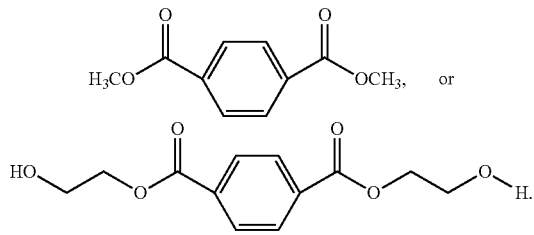

The following examples are intended to illustrate the disclosure more fully without limiting the scope, since numerous modifications and variations will be apparent to those skilled in this art.

Preparation of the Monomer Having a Structure Represented by Formula (I)

Preparation Example 1

Preparing N,N'-Bis(Carboxypentyl)Terephthalamide (BCTM) with Dimethyl Terephthalate and 6-Aminohexanoic Acid Sodium Salt 1 equivalent of 6-aminohexanoic acid (ACA), 1 equivalent of sodium hydroxide (NaOH), and suitable amount of water serving as solvent were added into a reaction bottle. After reacting for 2 hours, the reaction bottle was heated to remove the water, and then a solid mixture was obtained. Next, the solid mixture was dried at 90° C. for 12 hours in oven, and then solid 6-aminohexanoic acid sodium salt (ACA-Na) was obtained. Next, 0.97 g (0.005 mole) of dimethyl terephthalate (DMT), 2.32 g (0.015 mole) of dried 6-aminohexanoic acid sodium salt, and 20 ml of ethylene glycol (EG) were put into a reaction bottle. The reaction bottle was heated at 85-90° C. for 14 hours in the presence of nitrogen gas, and then cooled to room temperature and 20 ml of distilled water was added into it. After the solid reactant was dissolved, sulfuric acid aqueous solution (0.1M) was added dropwise slowly into the reaction bottle until the pH value of the solution was 6. Next, after the reaction bottle was set aside at room temperature for 20 hours, a solid precipitate was observed and collected to a glass bottle. Then, the solid precipitate was washed with 3 times weight of distilled water and filtered, and repeated 5 times these washing and filtration steps. Next, the washed solid was dried in an oven at 80° C., N,N'-bis(carboxypentyl)

BCTM

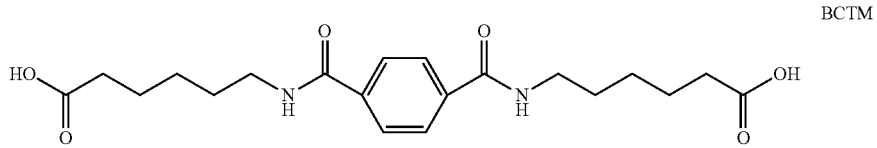 [SMILES: O=C(O)CCCCCNC(=O)c1ccc(C(=O)NCCCCCC(=O)O)cc1]

terephthalamide (BCTM) was obtained after drying. The above-mentioned reaction is represented as:

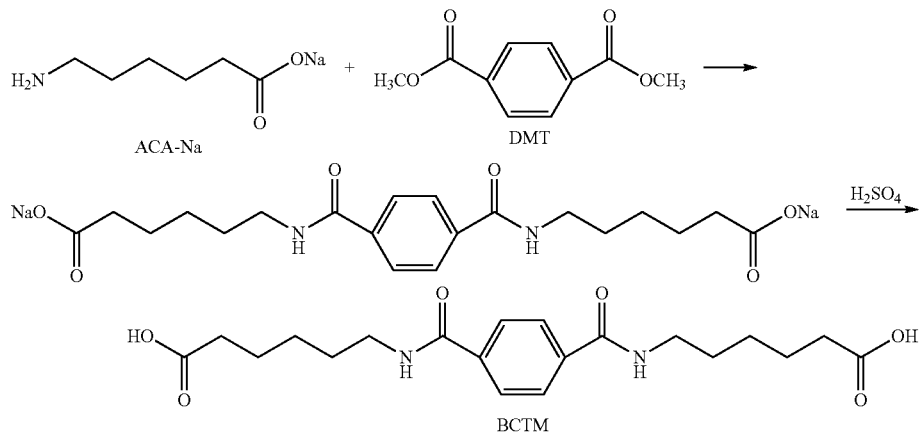

The N,N'-bis(carboxypentyl)terephthalamide was characterized by differential scanning calorimeter. The result shows that the N,N'-bis(carboxypentyl)terephthalamide has a melting temperature (Tm) at 204° C. (top peak). The N,N'-bis (carboxypentyl)terephthalamide was also analyzed by nuclear magnetic resonance spectroscopy (NMR) and infrared spectroscopy (IR). The spectrum data of N,N'-bis(carboxypentyl)terephthalamide is as follows:

$^1$H NMR (D$_2$SO$_4$, ppm): 8.53 (4H, phenyl-1,4-), 4.26 (4H, aromatic-CON—CH$_2$—, ACA), 3.52 (4H, aliphatic-CH$_2$—CO$_2$—, ACA), 1.88-2.37 (12H, aliphatic, ACA).

IR (cm$^{-1}$): 3308 (NH); 3300-2930 (broad, OH); 2858; 1725 (carbonyl of CO$_2$H); 1640 (amide); 1570-1350; 1300-800.

a reaction bottle. The reaction bottle was heated at 85-90° C. for 14 hours in the presence of nitrogen gas, and then cooled to room temperature and 20 ml of distilled water was added into it. After the solid reactant was dissolved, sulfuric acid aqueous solution (0.1M) was added dropwise slowly into the reaction bottle until the pH value of the solution was 6. Next, after the reaction bottle was set aside at room temperature for 20 hours, a solid precipitate was observed and collected to a glass bottle. Then, the solid precipitate was washed with 3 times weight of distilled water and filtered, and repeated 4 times these washing and filteration steps. Next, the washed solid was dried in an oven at 80° C., obtaining a N,N'-bis (carboxypentyl)terephthalamide (BCTM). The above-mentioned reaction is represented as:

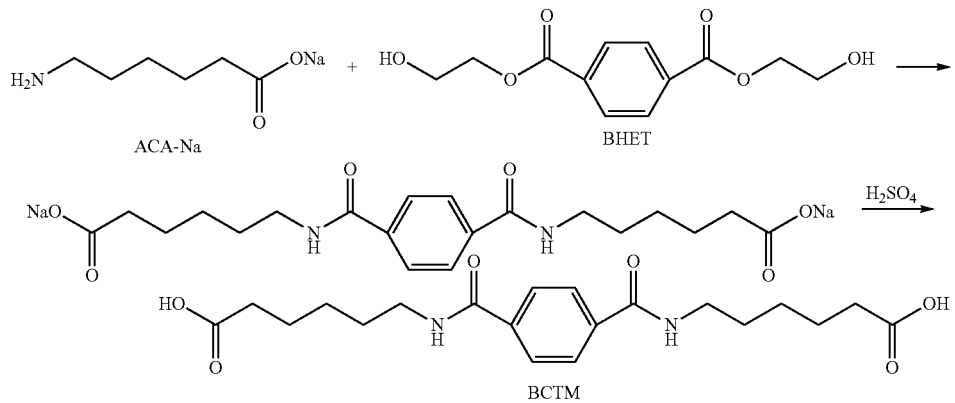

The results of integrating the spectrum data of NMR show that the molar ratio of

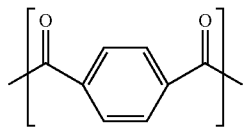

group and

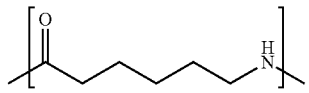

group of N,N'-bis(carboxypentyl)terephthalamide is 1:2.

Preparation Example 2

Preparing N,N'-Bis(Carboxypentyl)Terephthalamide (BCTM) with Bis-Hydroxylethyl Terephthalate and 6-Aminohexanoic Acid Sodium Salt—the Solution Reaction 3.84 g (0.005 mole) of bis-hydroxylethyl terephthalate (BHET), 2.32 g (0.015 mole) of dried 6-aminohexanoic acid sodium salt, and 20 ml of ethylene glycol (EG) were put into The N,N'-bis(carboxypentyl)terephthalamide obtained from preparation example 2 was characterized by differential scanning calorimeter. The result shows that the N,N'-bis(carboxypentyl)terephthalamide has a melting temperature (Tm) at 204° C. (top peak). The N,N'-bis(carboxypentyl)terephthalamide was also analyzed by nuclear magnetic resonance spectroscopy (NMR) and infrared spectroscopy (IR). The spectrum data of N,N'-bis(carboxypentyl)terephthalamide is the same as preparation example 1.

Preparation Example 3

Preparing N,N'-Bis(Carboxypentyl)Terephthalamide (BCTM) with Bis-Hydroxylethyl Terephthalate and 6-Aminohexanoic Acid Sodium Salt—the Melting Reaction 3.84 g (0.005 mole) of bis-hydroxylethyl terephthalate (BHET) and 2.32 g (0.015 mole) of dried 6-aminohexanoic acid sodium salt were put into a reaction bottle. The reaction bottle was heated at 195-200° C. for 14 hours in the presence of nitrogen gas, and then cooled to room temperature and 20 ml of distilled water was added into it. After the solid reactant was dissolved, sulfuric acid aqueous solution (0.1M) was added dropwise slowly into the reaction bottle until the pH value of the solution was 6. Next, after the reaction bottle was set aside at room temperature for 20 hours, a solid precipitate was observed and collected to a glass bottle. Then, the solid precipitate was washed with 3 times weight of distilled water and filtered, and repeated 4 times these washing and filteration steps. Next, the washed solid was dried in an oven at 80° C. The product was analyzed by nuclear magnetic resonance spectroscopy (NMR) and infrared spectroscopy (IR). The results show that the product includes N,N'-bis(carboxypentyl)terephthalamide (BCTM) which has the same spectrum as preparation example 1 and about 30% of by-product.

One method for synthesizing N,N'-bis(carboxypentyl)terephthalamide was carrying out by a reaction of 6-aminohexanoic acid and terephthaloyl chloride in the presence of hexamethylenediamine, pyridine, and N-methyl-2-pyrrolidone via a solution reaction, after purification then obtaining the product having the same spectrum as preparation example 1. (The above-mentioned reaction is represented as:

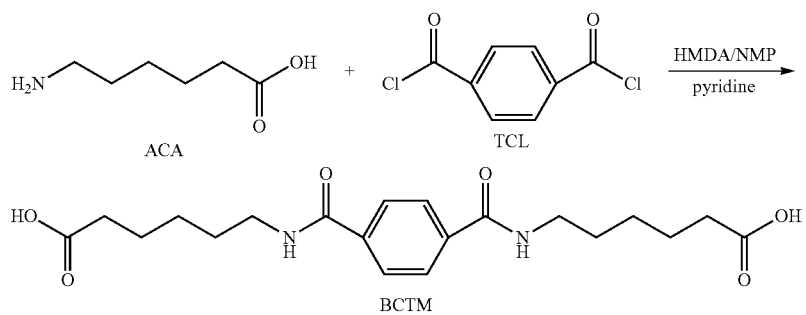

However, terephthaloyl chloride serving as an initiator of the reaction is an acyl chloride compound which is not an eco-friendly compound. So, the process using terephthaloyl chloride to form N,N'-bis(carboxypentyl)terephthalamide is not an eco-friendly process.

Comparative Preparation Example 1

0.97 g (0.005 mole) of dimethyl terephthalate (DMT), 1.69 g (0.015 mole) of 6-aminohexanoic acid (ACA), and 20 ml of ethylene glycol (EG) were put into a reaction bottle. The reaction bottle was heated at 85-90° C. for 14 hours in the presence of nitrogen gas, and then cooled to room temperature and 20 ml of distilled water was added into it. After the solid reactant was dissolved, sulfuric acid aqueous solution (0.1M) was added dropwise slowly into the reaction bottle until the pH value of the solution was 6. Next, after the reaction bottle was set aside at room temperature for 20 hours, a solid precipitate was observed and collected to a glass bottle. Then, the solid precipitate was washed with 3 times weight of distilled water and filtered, and repeated 4 times these washing and filteration steps. Because that 6-aminohexanoic acid would self-polymerize, and the product of self-polymerization would then react with dimethyl terephthalate, so the final product of the reaction would be a random copolymer rather than N,N'-bis(carboxypentyl)terephthalamide.

Preparation Example 4

Preparing N,N'-bis(6-aminohexyl)terephthalamide 0.97 g (0.005 mole) of dimethyl terephthalate (DMT), 3.06 g (0.02 mole) of hexamethylenediamine (HMDA), and 20 ml of ethylene glycol (EG) were put into a reaction bottle. The reaction bottle was heated at 85-90° C. for 14 hours in the presence of nitrogen gas, and then cooled to room temperature and 20 ml of distilled water was added into it. After the solid reactant was dissolved, sulfuric acid aqueous solution (0.1M) was added dropwise slowly into the reaction bottle until the pH value of the solution was 6. Next, after the reaction bottle was set aside at room temperature for 20 hours, a solid precipitate was observed and collected to a glass bottle. Then, the solid precipitate was washed with 3 times weight of distilled water and filtered, and repeated 4 times these washing and filtration steps Next, the washed solid was dried in an oven at 80° C., a solid N,N'-bis(6-aminohexyl)terephthalamide (BATM) was obtained after drying. The N,N'-bis(6-aminohexyl)terephthalamide was characterized by differential scanning calorimeter. The result shows that the N,N'-bis(6-aminohexyl)terephthalamide has a melting temperature (Tm) at 211° C. (top peak). The N,N'-bis(6-aminohexyl)terephthalamide was also analyzed by nuclear magnetic resonance spectroscopy (NMR) and infrared spectroscopy (IR). The spectrum data of N,N'-bis(6-aminohexyl)terephthalamide is as follows:

$^1$H NMR (D$_2$SO$_4$, ppm): 8.52 (4H, phenyl-1,4-), 4.26 (4H, aromatic-CON—CH$_2$—, HMDA), 3.91 (4H, aliphatic-CH$_2$—NH$_2$, HMDA), 1.88-2.37 (16H, aliphatic, HMDA).

IR (cm$^{-1}$): 3308-3294 (NH); 2927; 2858; 1643 (amide); 1570-1350; 1300-800.

The results of integrating the spectrum data of NMR show that the molar ratio of

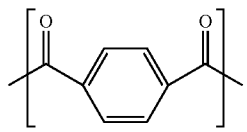

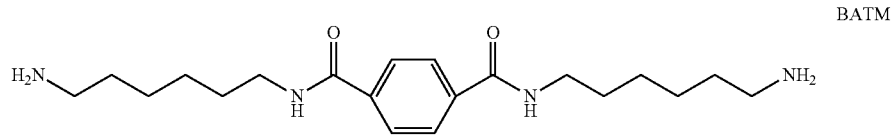 [SMILES: NCCCCCCNC(=O)c1ccc(C(=O)NCCCCCCN)cc1]

group and

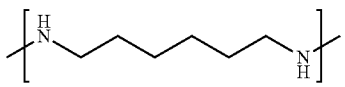

group of N,N'-bis(6-aminohexyl)terephthalamide is 1:2.

Preparation of Copolymer

Example 1

Preparing BCTM-Co-HMDA Copolymer 14.2 g (0.036 mole) of N,N'-bis(carboxypentyl)terephthalamide (BCTM), 4.2 g (0.036 mole) of hexamethylenediamine (HMDA), and 60 g of water were put into a reaction bottle. Next, the reaction bottle was heated to 85° C. After solid BCTM and HMDA were completely dissolved, the water was removed by vacuum distillation and the solid product was left in the reaction bottle. Next, the reaction bottle was heated slowly to 150° C. and maintained for 1 hour, heated at 180° C. for 2 hours, heated at 200° C. for 2 hours, and heated at 250° C. for 2 hours. After cooling, the resulting light brown solid of BCTM-co-HMDA copolymer which has a repeat unit represented by

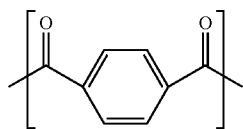

group,

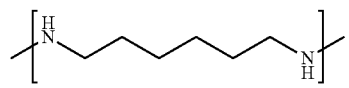

group, and

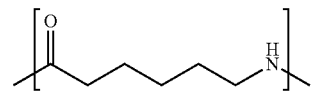

group of BCTM-co-HMDA copolymer is 1:1:2.

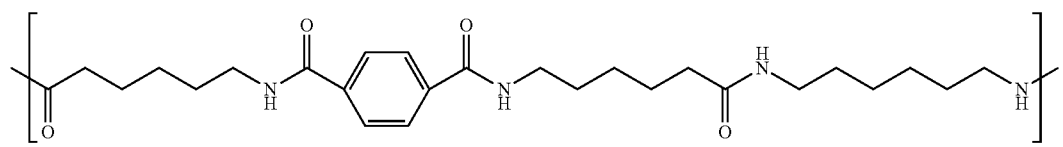

was obtained.

The BCTM-co-HMDA copolymer was characterized by differential scanning calorimeter. The results show that the BCTM-co-HMDA copolymer has a melting temperature (Tm) at 261° C. (top peak) and a glass transition temperature (Tg) at 75° C. The relative viscosity (R.V.) of BCTM-co-HMDA copolymer is 1.45. The steps of determining relative viscosity (R.V.) includes: providing 0.2 g of nylon copolymer in a glass bottle; adding concentrated sulfuric acid (concentration 97 wt %) into the glass bottle to form a 50 ml of solution; and, performing relative viscosity (R.V.) analysis at 25° C. The BCTM-co-HMDA copolymer was also analyzed by nuclear magnetic resonance spectroscopy (NMR) and infrared spectroscopy (IR). The spectrum data of BCTM-co-HMDA copolymer is as follows:

$^1$H NMR ($D_2SO_4$, ppm): 8.53 (4H, phenyl, BCTM), 4.26 (4H, aromatic-CON—$CH_2$—, ACA), 4.00 (4H, aliphatic-CON—$CH_2$—, HMDA), 3.18 (4H, aliphatic-$CH_2$—CON—, ACA), 1.87-2.34 (20H, aliphatic, ACA and HMDA).

$^{13}$C NMR ($D_2SO_4$, ppm): 178 and 172 (amide), 131 (aromatic), 44-43, 33, 27-24.

IR ($cm^{-1}$): 3304 (NH); 2930; 2858; 1630 (broad, amide); 1570-1350; 1300-800.

The results of integrating the spectrum data of NMR show that the molar ratio of The steps of Example 1 were repeated twice as Verification 1 and Verification 2. The BCTM-co-HMDA copolymer obtained from Verification 1 and Verification 2 were characterized by differential scanning calorimeter. The results show that the BCTM-co-HMDA copolymer obtained from Verification 1 and Verification 2 respectively has a melting temperature (Tm) at 262° C. and 261° C. (top peak), and a glass transition temperature (Tg) at 74-75° C. The BCTM-co-HMDA copolymer obtained from Verification 1 and Verification 2 were also analyzed by nuclear magnetic resonance spectroscopy (NMR) and infrared spectroscopy (IR). The spectrum data of BCTM-co-HMDA copolymer obtained from Verification 1 and Verification 2 is the same as Example 1, showing that the reproducibility of chemical structure and physical properties is good.

Example 2

Preparing BCTM-Co-TMDA Copolymer

The similar steps as Example 1 were carried out while using 3.18 g of tetramethylene diamine (TMDA) to replace 4.2 g of hexamethylenediamine (HMDA), obtaining a BCTM-co-TMDA copolymer having a repeat unit represented by

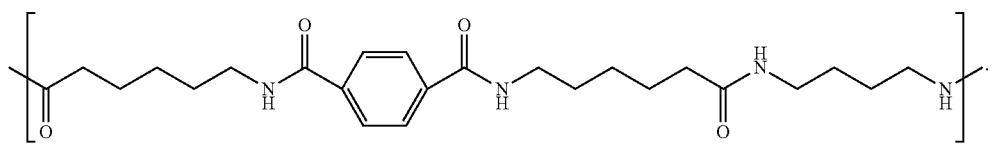

The BCTM-co-TMDA copolymer was characterized by differential scanning calorimeter. The result shows that the BCTM-co-TMDA copolymer has a melting temperature (Tm) at 263° C. (top peak) and a glass transition temperature (Tg) at 76° C. The relative viscosity (R.V.) of BCTM-co-

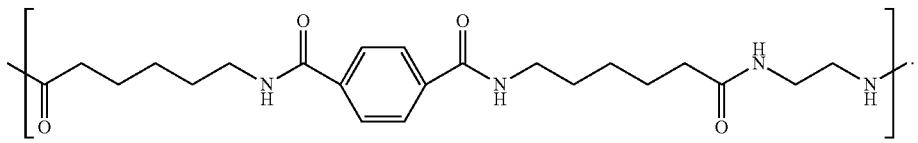

TMDA copolymer is 1.52. The BCTM-co-TMDA copolymer was also analyzed by nuclear magnetic resonance spectroscopy (NMR) and infrared spectroscopy (IR). The spectrum data of BCTM-co-TMDA copolymer is as follows:

$^1$H NMR (D$_2$SO$_4$, ppm): 8.53 (4H, phenyl, BCTM), 4.26 (4H, aromatic-CON—CH$_2$—, ACA), 4.00 (4H, aliphatic-CON—CH$_2$—, TMDA), 3.18 (4H, aliphatic-CH$_2$—CON—, ACA), 1.87-2.34 (16H, aliphatic, ACA and TMDA).

$^{13}$C NMR (D$_2$SO$_4$, ppm): 178 and 173 (amide), 131 (aromatic), 44-43, 33, 27-24.

IR (cm$^{-1}$): 3304 (NH); 2930; 2858; 1630 (broad, amide); 1570-1350; 1300-800.

The results of integrating the spectrum data of NMR show that the molar ratio of

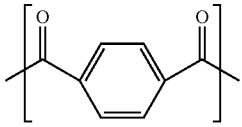

group,

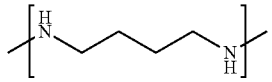

group, and group of BCTM-co-TMDA copolymer is 1:1:2.

Example 3

Preparing BCTM-Co-EDA Copolymer

The similar steps as Example 1 were carried out while using 2.17 g of ethylene diamine (EDA) to replace 4.2 g of hexamethylenediamine (HMDA), obtaining a BCTM-co-EDA copolymer having a repeat unit represented by The BCTM-co-EDA copolymer was analyzed by nuclear magnetic resonance spectroscopy (NMR) and infrared spectroscopy (IR). The spectrum data of BCTM-co-EDA copolymer is as follows:

$^1$H NMR (D$_2$SO$_4$, ppm): 8.53 (4H, phenyl, BCTM), 4.26 (4H, aromatic-CON—CH$_2$—, ACA), 4.10 (4H, aliphatic-CON—CH$_2$—, EDA), 3.18 (4H, aliphatic-CH$_2$—CON—, ACA), 1.87-2.34 (12H, aliphatic, ACA).

$^{13}$C NMR (D$_2$SO$_4$, ppm): 178 and 173 (amide), 131 (aromatic), 44-43, 33, 27-24.

IR (cm$^{-1}$): 3309 (NH); 2930; 2855; 1630 (broad, amide); 1570-1350; 1300-800.

The results of integrating the spectrum data of NMR show that the molar ratio of

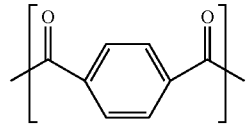

group,

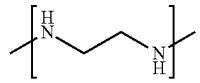

group, and group of BCTM-co-EDA copolymer is 1:1:2.

Example 4

Preparing BCTM-Co-PDA Copolymer

The similar steps as Example 1 were carried out while using 3.91 g of para-phenylenediamine (PDA) to replace 4.2 g of hexamethylenediamine (HMDA), obtaining a BCTM-co-PDA copolymer having a repeat unit represented by

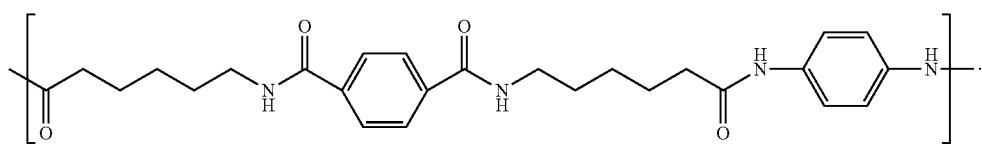

The BCTM-co-PDA copolymer was analyzed by nuclear magnetic resonance spectroscopy (NMR) and infrared spectroscopy (IR). The spectrum data of BCTM-co-PDA copolymer is as follows:

$^1$H NMR (D$_2$SO$_4$, ppm): 8.53 (4H, phenyl, BCTM), 7.11 (4H, phenyl, PDA), 4.26 (4H, aromatic-CON—CH$_2$—, ACA), 3.18 (4H, aliphatic-CH$_2$—CON—, ACA), 1.87-2.34 (12H, aliphatic, ACA).

IR (cm$^{-1}$): 3309-3270 (NH); 2920; 2861; 1645 (broad, amide); 1590-1350; 1300-800.

The results of integrating the spectrum data of NMR show that the molar ratio of

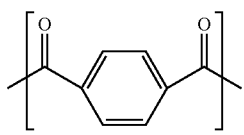

group,

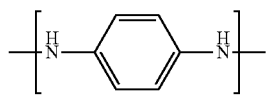

group, and

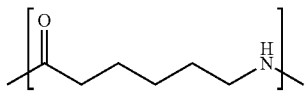

group of BCTM-co-PDA copolymer is 1:1:1.8-1.9.

Example 5

Preparing BCTM-Co-BHET Copolymer

The similar steps as Example 1 were carried out while using 31.38 g of bis-hydroxylethyl terephthalate tetramer

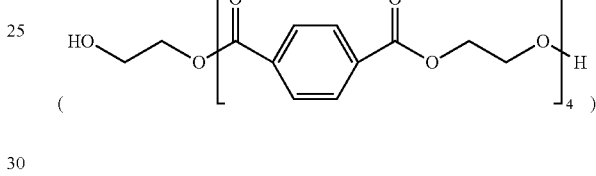

to replace 4.2 g of hexamethylenediamine (HMDA), obtaining a BCTM-co-BHET copolymer having a repeat unit represented by

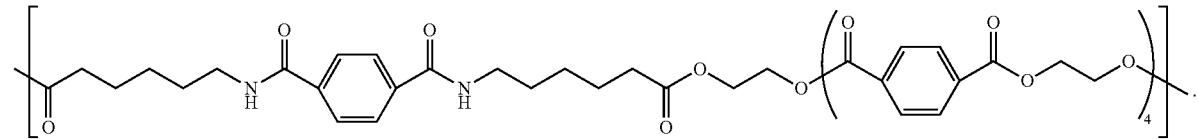

The BCTM-co-BHET copolymer was characterized by differential scanning calorimeter. The result shows that the BCTM-co-BHET copolymer has a melting temperature (Tm) at 247° C. (top peak).

Example 6

Preparing BATM-Co-AA Copolymer 12.98 g (0.036 mole) of N,N'-bis(6-aminohexyl)terephthalamide (BATM), 5.29 g (0.036 mole) of adipic acid (AA), and 60 g of water were put into a reaction bottle in the presence of nitrogen gas. Next, the reaction bottle was heated to achieve 85° C. After solid BATM and AA were completely dissolved, the water was removed by vacuum distillation and the solid product was leaved in the reaction bottle. Next, the reaction bottle was heated slowly to 150° C. and maintained for 1 hour, heated at 180° C. for 2 hours, heated at 200° C. for 2 hours, and heated at 250° C. for 2 hours. After cooling, a BATM-co-AA copolymer having a repeat unit represented by

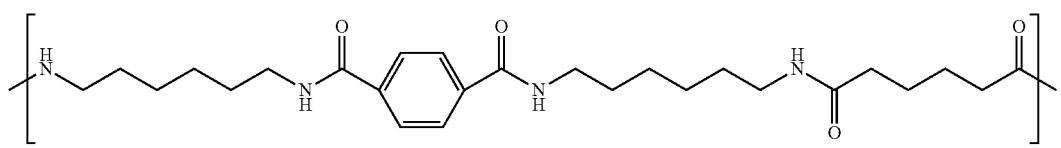

was obtained.

The BATM-co-AA copolymer was characterized by differential scanning calorimeter. The result shows that the BATM-co-AA copolymer has a melting temperature (Tm) at 301° C. (top peak) and a glass transition temperature (Tg) at 78° C. The relative viscosity (R.V.) of BATM-co-AA copolymer is 1.52. The BATM-co-AA copolymer was also analyzed by nuclear magnetic resonance spectroscopy (NMR) and infrared spectroscopy (IR). The spectrum data of BATM-co-AA copolymer is as follows:

$^1$H NMR (D$_2$SO$_4$, ppm): 8.53 (4H, phenyl, BATM), 4.26 (4H, aromatic-CON—CH$_2$—, HMDA), 4.00 (4H, aliphatic-CON—CH$_2$—, HMDA), 3.18 (4H, aliphatic-CH$_2$—CON—, AA), 1.86-2.36 (20H, aliphatic, HMDA and AA).

Example 7 preparing BATM-co-IPA copolymer 12.98 g (0.036 mole) of N,N'-bis(6-aminohexyl)terephthalamide (BATM), 6.02 g (0.036 mole) of isophthalic acid (IPA), and 60 g of water were put into a reaction bottle. Next, the reaction bottle was heated to 85° C. After solid BATM and IPA were completely dissolved, the water was removed by vacuum distillation and the solid product was left in the reaction bottle. Next, the reaction bottle was heated slowly to 150° C. and maintained for 1 hour, heated at 180° C. for 2 hours, heated at 200° C. for 2 hours, and heated at 250° C. for 2 hours. After cooling, a BATM-co-IPA copolymer having a repeat unit represented by

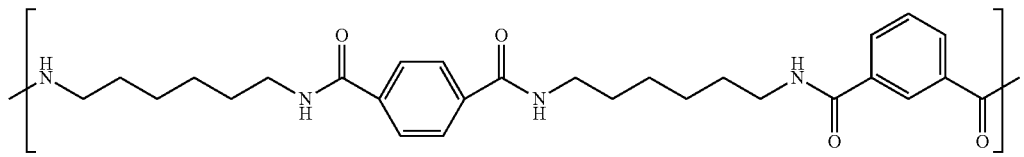

was obtained.

The BATM-co-IPA copolymer was characterized by differential scanning calorimeter. The result shows that the BATM-co-IPA copolymer has a non-obvious melting temperature (Tm) and a glass transition temperature (Tg) at 115° C. The relative viscosity (R.V.) of BATM-co-IPA copolymer is 1.41. The BATM-co-IPA copolymer was also analyzed by nuclear magnetic resonance spectroscopy (NMR) and infrared spectroscopy (IR). The spectrum data of BATM-co-IPA copolymer is as follows:

$^1$H NMR (D$_2$SO$_4$, ppm): 9.02 (1H, phenyl, IPA), 8.53 (4H, phenyl, BATM), 8.45 (2H, phenyl, IPA), 7.96 (1H, phenyl, IPA), 4.26 (4H, aromatic-CON—CH$_2$—, HMDA), 4.00 (4H, aliphatic-CON—CH$_2$—, HMDA), 1.86-2.36 (8H, aliphatic, HMDA).

$^{13}$C NMR (D$_2$SO$_4$, ppm): 177 and 175 (amide), 140, 132, 129 (aromatic), 44-43, 28-24.

IR (cm$^{-1}$): 3305-3300 (NH); 2930; 2878; 1676 (broad, amide); 1570-800.

The results of integrating the spectrum data of NMR show that the molar ratio of

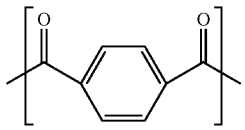

group, $^{13}$C NMR (D$_2$SO$_4$, ppm): 177 and 172 (amide), 131 (aromatic), 44-43, 32, 28-24.

IR (cm$^{-1}$): 3302 (NH); 2930; 2855; 1630 (broad, amide); 1570-1350; 1300-800.

The results of integrating the spectrum data of NMR show that the molar ratio of

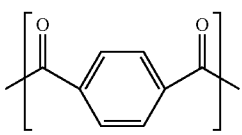

group,

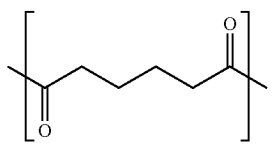

group, and

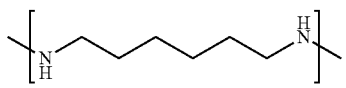

group of BATM-co-AA copolymer is 1:1:2.

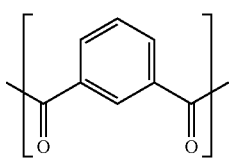

group, and

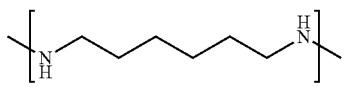

group of BATM-co-IPA copolymer is 1:1:2.

Comparative Example 1

A melting polymerization of hexamethylenediamine (HMDA), terephthalic acid (TPA), and caprolactam (CPL) was carried out according to the general synthesis method of nylon copolymer disclosed in "Rwei, S. P. et al., Thermochimica Acta, 555, 37-45, 2013", obtaining copolymer (1).

The copolymer (1) was characterized by differential scanning calorimeter. The result shows that the copolymer (1) has two peak value, respectively 183° C. and 213° C., corresponding to melting temperature (Tm). The relative viscosity (R.V.) of copolymer (1) is 2.0. The copolymer (1) was also analyzed by nuclear magnetic resonance spectroscopy (NMR) and infrared spectroscopy (IR). The spectrum data of copolymer (1) is as follows:

$^1$H NMR: δ 8.53 (4H, phenyl), 4.26 (4H, aromatic-CON—CH$_2$), 4.00 (4H, aliphatic-CON—CH$_2$), 3.18 (4H, aliphatic-CH$_2$—CON), 1.87-2.34 (aliphatic, CPL and HMDA).

$^{13}$C NMR (D$_2$SO$_4$, ppm): 178 and 172 (amide), 131 (aromatic), 44-43, 33, 27-24.

IR (cm$^{-1}$): 3304 (NH); 2930; 2861; 1630 (broad, amide); 1570-800.

Because of the absorption peaks of CPL and HMDA in spectrum are very similar, there are many overlaps between them. So the repeat unit ratio was determined according to the aromatic and aliphatic peaks of the spectrum data. The results show that the molar ratio of aromatic group

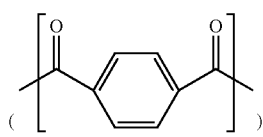

and aliphatic group

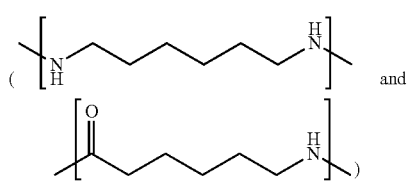

is 1.00:2.97.

Comparative Example 2

The steps of Comparative Example 1 were repeated for verification, obtaining copolymer (2). The copolymer (2) was characterized by differential scanning calorimeter. The result shows that the copolymer (1) has melting temperature (Tm) between 190° C. and 220° C. (broad peak). The copolymer (2) was also analyzed by nuclear magnetic resonance spectroscopy (NMR) and infrared spectroscopy (IR). The spectrum data of copolymer (2) is as follows:

$^1$H NMR: δ 8.53 (4H, phenyl), 4.26 (4H, aromatic-CON—CH$_2$), 4.00 (4H, aliphatic-CON—CH$_2$), 3.18 (4H, aliphatic-CH$_2$—CON), 1.87-2.34 (aliphatic, CPL and HMDA).

$^{13}$C NMR (D$_2$SO$_4$, ppm): δ 178 and 172 (amide), 131 (aromatic), 44-43, 33, 27-24.

IR (cm$^{-1}$): 3304 (NH); 2930; 2861; 1630 (broad, amide); 1570-800.

The repeat unit ratio was determined according to the aromatic and aliphatic peaks of the spectrum data. The results show that the molar ratio of aromatic group

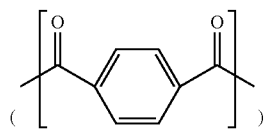

and aliphatic group

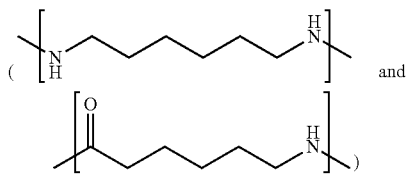

of copolymer (2) is 1.00:2.98.

Comparative Example 3

The steps of Comparative Example 1 were repeated for verification, obtaining copolymer (3). The copolymer (3) was characterized by differential scanning calorimeter. The result shows that the copolymer (3) has melting temperature (Tm) at 185° C., 192° C. and 218° C. The copolymer (3) was also analyzed by nuclear magnetic resonance spectroscopy (NMR) and infrared spectroscopy (IR). The spectrum data of copolymer (3) is as follows:

$^1$H NMR: δ 8.53 (4H, phenyl), 4.26 (4H, aromatic-CON—CH$_2$), 4.00 (4H, aliphatic-CON—CH$_2$), 3.18 (4H, aliphatic-CH$_2$—CON), 1.87-2.34 (aliphatic, CPL and HMDA).

$^{13}$C NMR (D$_2$SO$_4$, ppm): 178 and 172 (amide), 131 (aromatic), 44-43, 33, 27-24.

IR (cm$^{-1}$): 3304 (NH); 2930; 2861; 1630 (broad, amide); 1570-800.

The repeat unit ratio was determined according to the aromatic and aliphatic peaks of the spectrum data. The results show that the molar ratio of aromatic group

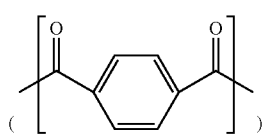

and aliphatic group

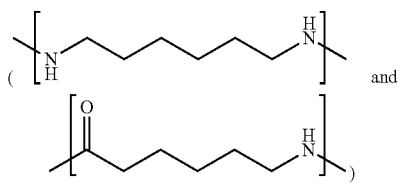

of copolymer (3) is 1.00:2.98.

Comparative Example 4

According to the general synthesis method of nylon copolymer disclosed in "Rwei, S. P. et al., Thermochimica Acta, 555, 37-45, 2013". The mixture of 0.8 kg of caprolactam, 0.16 kg of water, and 0.06 kg of acetic acid was heated at 180° C. for 2 hours, heated at 200° C. for 2 hours, and heated slowly to 260° C. in 2 hours and maintained the temperature for 6 hours. After cooling down, feeding and pelleting, a nylon 6 polymer was obtained.

Next, the products of Example 1, Verification 1, Verification 2, and Comparative Examples 1-4 were subjected to a hot water extractable amount test, and the results are shown in Table 1. The steps of the hot water extractable amount test include: placing the analyte in a reaction bottle (the weight of the analyte is W0); adding 15 times of W0 of water; heating and refluxing for 10 hours; removing the solution; collecting, drying, and weighting the rest solid (the weight of the rest solid is W1); and calculating the hot water extractable amount with the following equation: (W0−W1)/W0×100 wt %.

TABLE 1

| | Adding Amount of Group- Before Reaction (Molar Ratio) | | | Containing Amount of Group of Copolymer- After Reaction (Molar Ratio) | | | $T_g$ (° C.) | Tm (° C.) | Hot Water Extractable Amount (wt %) |
|---|---|---|---|---|---|---|---|---|---|
| | CPL | TPA | HMDA | CPL | TPA | HMDA | | | |
| Example 1 | 50 | 25 | 25 | 50 | 25 | 25 | 75 | 261 | 2.0 |
| Example 1-Verification 1 | 50 | 25 | 25 | 50 | 25 | 25 | 74 | 262 | 1.8 |
| Example 1-Verification 2 | 50 | 25 | 25 | 50 | 25 | 25 | 75 | 261 | 1.9 |
| Comparative Example 1 | 50 | 25 | 25 | CPL + HMDA = 74.25 | 25 | CPL + HMDA = 74.25 | 45 | 183; 213 | 3.2 |
| Comparative Example 2 | 50 | 25 | 25 | CPL + HMDA = 74.50 | 25 | CPL + HMDA = 74.50 | 41 | 190-220 (broad peak) | 3.5 |
| Comparative Example 3 | 50 | 25 | 25 | CPL + HMDA = 74.50 | 25 | CPL + HMDA = 74.50 | 51 | 185; 192 (broad peak) | 3.2 |
| Comparative Example 4 (Nylon 6) | 100 | — | — | | | | 49 | 225 | 8.2 |

| | Adding Amount of Group- Before Reaction (Molar Ratio) | | | Containing Amount of Group of Copolymer- After Reaction (Molar Ratio) | | | $T_g$ (° C.) | Tm (° C.) | Hot Water Extractable Amount (wt %) |
|---|---|---|---|---|---|---|---|---|---|
| | AA | HMDA | — | AA | HMDA | — | | | |
| Nylon 66 (BASF) | 50 | 50 | — | | | | 54 | 265 | — |

Remark: CPL is

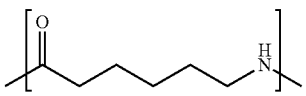

group, TPA is

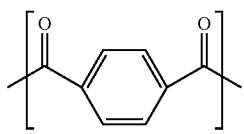

group, HMDA is

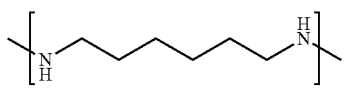

group, and AA is

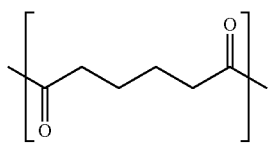

group.

As shown in Table 1, although hexamethylenediamine (HMDA), terephthalic acid (TPA), and caprolactam (CPL) serve as reactive monomers and carry out a copolymerization reaction with the same steps (Comparative Examples 1-3), the obtained copolymers (1)-(3) have different structure (or different molar ratio of repeat units) and exhibit different properties (such as melting temperature and transition temperature). Due to a conventional method of copolymerizaion was used in Comparative Examples 1-3, the product of the copolymerization reaction within the three monomers, which are HMDA, TPA, and CPL, possess many different arrangements, so the products of the copolymerization reaction are random copolymers constituting in different group permutations and different molecular weights. Besides, the divergence between hexamethylenediamine of aromatic moiety and terephthalic acid of aliphatic moiety, includes low compatibility and large reactive difference of end functional group, cause sequential distribution of terephthalic acid in molecular main chain is unevenly. Therefore, the copolymer has lower structure regularity and without reproducibility of chemical structure and properties. Accordingly, it is difficult to obtain copolymers having similar chemical structures and properties by means of the conventional method. In contrast, as the results of Example 1, Verification 1, and Verification 2 show that adding amount of monomers before the reaction and containing amount of the derivatives of monomers in the of copolymer after the reaction are almost the same, due to the good sequential distribution of the monomer having the structure represented by Formula (I) in molecular main chain is evenly. It is because that the reaction sequence of the method of the present disclosure is as follows: first, the reaction of the monomer having

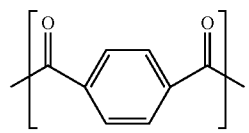

group and the monomer having

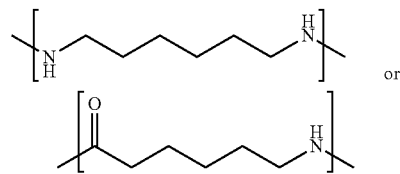

group, which are randomly distributed in the molecular main chain with the conventional method, is carried out to obtain the comonomer having the structure represented by Formula (I); then, the comonomer and the monomer having the structure represented by Formula (II) are copolymerized in alternative copolymerization form, and the alternative copolymer is then obtained. This method can improve the compatibility and lower reactive difference of end functional group between the comonomers having the structure represented by Formula (I) and the monomer having the structure represented by Formula (II). Hence, the uniformity of sequential distribution of

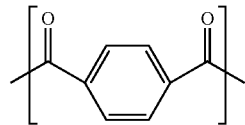

group in copolymer main chain is improved and a nearly alternative copolymer is obtained, such as the copolymer obtained in Example 1 having a repeat unit represented by

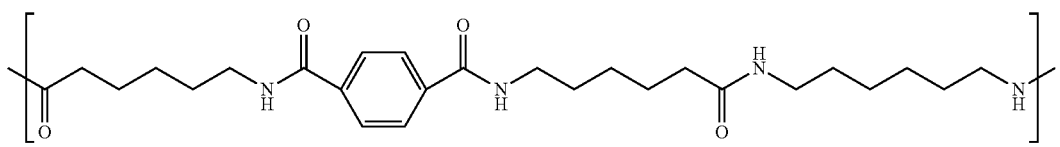

that the sequential distribution of groups in main chain is [-CPL-TPA-CPL-HMDA-] (CPL is

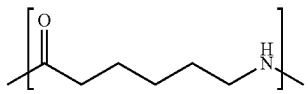

group, TPA is

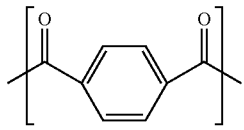

group, HMDA is

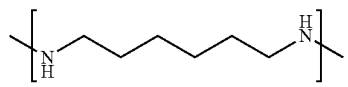

group, and AA is

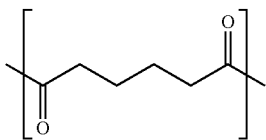

group). Accordingly, comparing to the conventional method, the method of the present disclosure can improve symmetry and sequential distribution of molecular structure and properties such as melting temperature of the copolymer product. When the copolymer product of the present disclosure applied in processing process of plastics and fibers can improve stability, reduce filament breaking rate, and lower variability of products.

In addition, comparing to nylon 6 obtained from commercial method and the copolymers obtained from Comparative Examples 1-4, the copolymers obtained from Example 1, Verification 1, and Verification 2 exhibit significantly improvements at melting temperature and transition temperature. The transition temperature of the copolymers obtained from Example 1, Verification 1, and Verification 2 are 20-30° C. higher than that of nylon 6 and nylon 66 obtained from commercial method, and the melting temperature of the copolymers obtained from Example 1, Verification 1, and Verification 2 are near to that of nylon 66 obtained from commercial method. Furthermore, the hot water extractable amount of the copolymers obtained from Example 1, Verification 1, and Verification 2 are lower than that of nylon 6 obtained from commercial method and the copolymers obtained from Comparative Examples 1-3.

Consequently, as shown in Table 1, the copolymer of the present disclosure has properties much better than that of nylon 6. Further, comparing to nylon 66, the copolymer of the present disclosure has

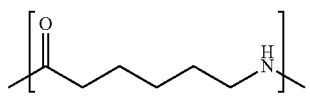

group more than 49 mole %, and has Tm and Tg near to or better than nylon 66. Therefore, the copolymer of the present disclosure has chance to replace the existing applications of nylon 66. As the results of Example 1, Verification 1, and Verification 2, the copolymer of the present disclosure has high reproducibility, i.e. similar chemical structure and properties, and suitable for commercialize, because the stability of properties is an important requirement in commercialize, that is, every batch copolymer products have same properties.

It will be apparent to those skilled in the art that various modifications and variations can be made to the disclosed methods and materials. It is intended that the specification and examples be considered as exemplary only, with a true scope of the disclosure being indicated by the following claims and their equivalents.

What is claimed is:

1. A copolymer, which is a reaction product of a first monomer and a second monomer, wherein the first monomer has a structure represented by Formula (I)

Formula (I)

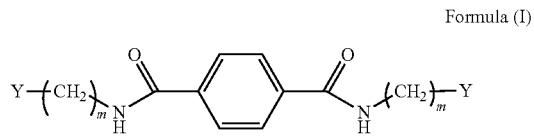

wherein Y is —NH$_2$, or —CO$_2$H; m is a positive integer from 2 to 10; when Y is —CO$_2$H, the second monomer has a structure represented by Formula (II), or Formula (III), and when Y is —NH$_2$, the second monomer has a structure represented by Formula (IV)

X—A—X  Formula (II)

Formula (III)

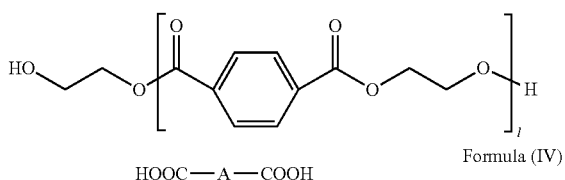

Formula (IV)

HOOC—A—COOH

Wherein X is independently —NH$_2$, or —OH; A is $-\!\!\left(\!CH_2\!\right)_{\!n}\!-$,

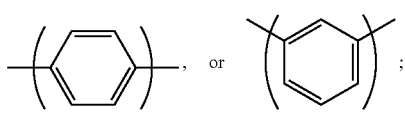

n is a positive integer from 2 to 10; and, l is a positive integer from 1 to 5.

2. The copolymer as claimed in claim 1, wherein the first monomer is

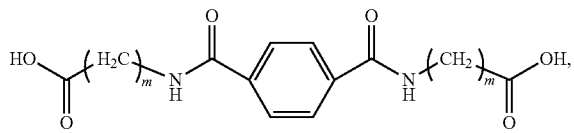

wherein m is a positive integer from 2 to 10.

3. The copolymer as claimed in claim 2, wherein the second monomer is $H_2N$-A-$NH_2$, wherein, A is $-(CH_2)_n$,

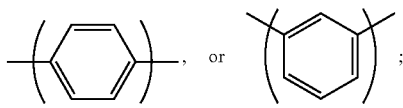

and, n is a positive integer from 2 to 10.

4. The copolymer as claimed in claim 3, wherein the second monomer is

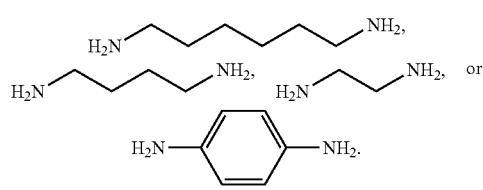

5. The copolymer as claimed in claim 2, wherein the second monomer is

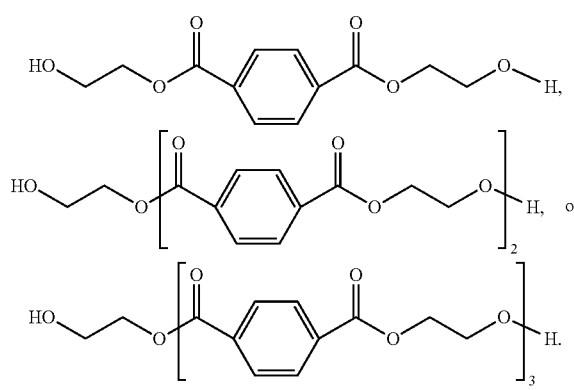

6. The copolymer as claimed in claim 1, wherein the first monomer is

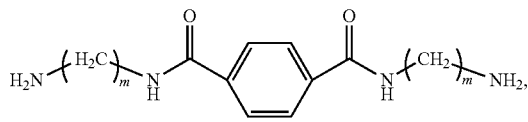

wherein m is a positive integer from 2 to 10.

7. The copolymer as claimed in claim 6, wherein the second monomer is

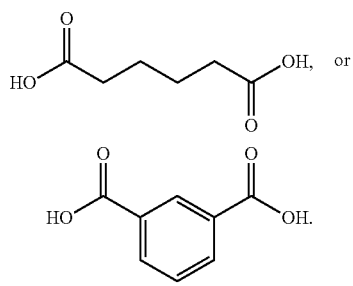

8. The copolymer as claimed in claim 1, wherein the copolymer has a repeat unit represented by Formula (V):

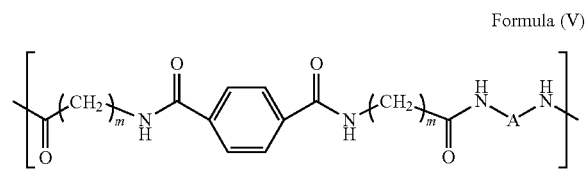

wherein A is $-(CH_2)_n$,

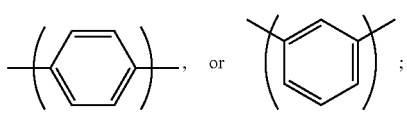

m is a positive integer from 2 to 10; and, n is a positive integer from 2 to 10.

9. The copolymer as claimed in claim 1, wherein the copolymer has a repeat unit represented by Formula (VI):

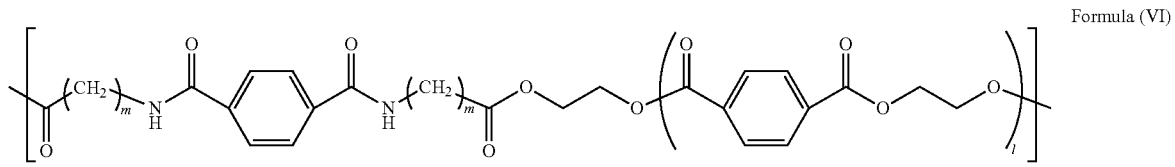

wherein m is a positive integer from 2 to 10; and, 1 is a positive integer from 1 to 5.

10. The copolymer as claimed in claim 1, wherein the copolymer has a repeat unit represented by Formula (VII):

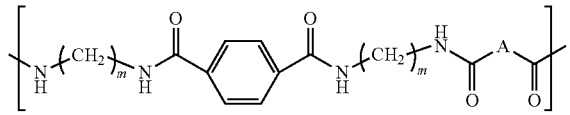

Formula (VII)

wherein A is $-(CH_2)_n$,

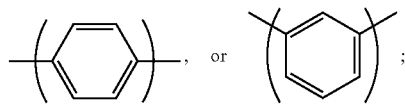

m is a positive integer from 2 to 10; and, n is a positive integer from 2 to 10.

11. The copolymer as claimed in claim 1, wherein the copolymer has a melting temperature between 220° C. to 270° C.

12. A method for preparing a monomer, comprising:
reacting a compound having a structure represented by Formula (VIII) and a compound having a structure represented by Formula (IX) via a melting reaction or a solution reaction; and
subjecting a reaction product of the melting reaction or the solution reaction to a acidification reaction to obtain the monomer having a structure represented by Formula (I):

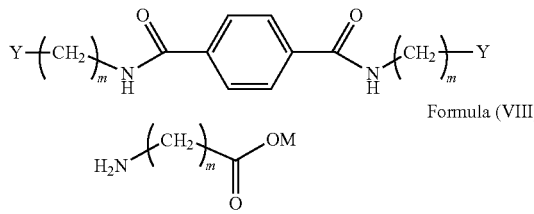

Formula (I)

Formula (VIII)

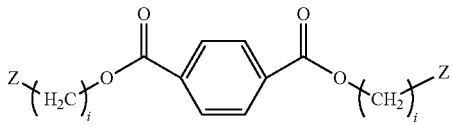

Formula (IX)

wherein M is Na, or K; m is a positive integer from 2 to 10; i is a positive integer from 1 to 3; Y is —CO$_2$H; and, Z is H or —OH.

13. The method as claimed in claim 12, wherein the solution reaction is carried out with a temperature between 85° C. and 95° C.

14. The method as claimed in claim 12, wherein the melting reaction is carried out with a temperature between 190° C. and 210° C.

15. The method as claimed in claim 12, wherein the acidification reaction comprising:
mixing the reaction product and water to form a mixture; and
titrating the mixture with an inorganic acid aqueous solution until that the mixture has a pH value between 5 and 7.

16. The method as claimed in claim 12, wherein the compound having a structure represented by Formula (VIII) is

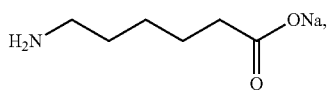

and the compound having a structure represented by Formula (IX) is

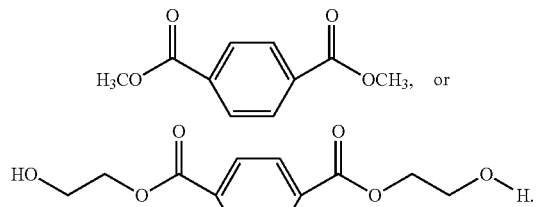

* * * * *